US006415659B1

United States Patent
Mioduszewski et al.

(10) Patent No.: US 6,415,659 B1
(45) Date of Patent: Jul. 9, 2002

(54) METHOD FOR ANALYZING PURGE WATER

(75) Inventors: David Mioduszewski; David A. Fischer, both of Ann Arbor, MI (US); David B. Kaminski, Clayton, CA (US)

(73) Assignee: QED Environmental Systems, Inc., Ann Arbor, MI (US)

( * ) Notice: Subject to any disclaimer, the term of this patent is extended or adjusted under 35 U.S.C. 154(b) by 6 days.

(21) Appl. No.: 09/660,619

(22) Filed: Sep. 13, 2000

(51) Int. Cl.[7] .......................... E21B 49/00; E21B 49/08; G01N 1/00; G01N 1/14
(52) U.S. Cl. .................. 73/152.23; 73/863.01; 73/863.83
(58) Field of Search .................. 73/152.18, 152.23, 73/863.01, 863.83; 436/28, 39, 163

(56) References Cited

U.S. PATENT DOCUMENTS

| | | | | |
|---|---|---|---|---|
| 4,669,554 A | * | 6/1987 | Cordry | 175/59 |
| 4,717,473 A | * | 1/1988 | Burge et al. | 210/170 |
| 4,765,182 A | * | 8/1988 | Boone | 73/153 |
| 5,329,811 A | * | 7/1994 | Schultz et al. | 73/155 |
| 5,561,245 A | * | 10/1996 | Georgi et al. | 73/152.02 |
| 5,794,696 A | * | 8/1998 | Gibson et al. | 166/264 |

OTHER PUBLICATIONS

"User's Guide" published prior to filing date Sep. 13, 2000. Paper entitled "Model 6000 Static Water Level Meter" dated Jun. 16, 1992.
"Electronic Programmable Controller Model 400" published prior to filing date of Sep. 13, 2000.
"FC 5000 Flow Cell Meter & Sonde Quickguide" published Oct. 20, 1999.
Information Sheet "Low Flow Ground Water Sampling" issued Jun. 1996 from the Maine Department of Environmental Protection.
EPA Ground Water Issue Low–Flow (Minimal Drawdown) Ground–Water Sampling Procedures issued Dec. 1995 from U.S. Environment Protection Agency.

* cited by examiner

Primary Examiner—Hezron Williams
Assistant Examiner—Katina Wilson
(74) Attorney, Agent, or Firm—Harness, Dickey & Pierce, PLC

(57) ABSTRACT

The present invention provides a method for monitoring select purge water parameters and determining when the parameters have stabilized. The method includes the steps of selecting which parameters are to be monitored and selecting the time interval between which evaluation readings are performed. The time interval may be selected in set time increments from within a predetermined time range. With the passing of each interval, the results of the evaluation readings are stored in a memory device for at least one, and more preferably a plurality, of consecutive readings. If the readings do not fall within the defined stabilization ranges for the selected parameters, the oldest scan is deleted from the memory device. The comparison of the reading results is again performed with the start of the next interval, with the new reading results being compared to the two old reading results. When the selected parameter values do fall within the defined ranges for three consecutive readings, the operator is alerted that stabilization has been obtained.

13 Claims, 3 Drawing Sheets

METHOD FOR ANALYZING PURGE WATER

BACKGROUND OF THE INVENTION

1. Technical Field

The present invention generally pertains to the monitoring of ground water quality. More specifically, the present invention relates to a method for monitoring ground water purged using low-flow techniques wherein the stabilization of select water parameters is monitored and analyzed.

2. Discussion

Heightened awareness of the dangers of subsurface water pollution has resulted in the development of improved techniques for obtaining and analyzing subsurface water quality. Originally, water to be analyzed was purged from a well casing using bailers or high speed pumps. Using this method three to five casing volumes of water were removed from a well, and from this water the sample to be analyzed was collected. However, this method often adversely impacted upon sample quality due to the collection of samples with high levels of turbidity. Such samples often included immobile foreign particles which were not representative of the water in the vicinity of the well and which produced an overestimation of certain substances of interest, such as metals or hydrophobic organic compounds.

In an attempt to rectify the turbidity problem, filtration was often implemented with less than desirable results. Filtration was found to remove potentially mobile contaminant-associated particles, thus resulting in artificially low contaminant concentrations. It is now generally accepted that water in a well casing is not necessarily representative of the water generally contained in the ground surrounding the well, which is known as the formation water. However, it has been found that water within the screened interval of a well may be representative of the formation water.

The emergence of low-flow purging and sampling techniques have substantially diminished the turbidity problems described above and minimized the mixing between the overlying stagnant casing water and the water within the screened interval. Low flow does not refer to the flow rate of water discharged at the surface, but instead refers to the velocity with which water enters the pump intake. Low flow purging is typically performed using a pump-intake located in the middle or slightly above the middle of the screened interval of the well. This is done because if the pump is placed too close to the bottom of the well, the purging will cause the unwanted uptake of solids which have collected at the bottom of the well.

In order to ensure that the water pumped from the well is representative of the formation water rather than the stagnant water of the well casing, various parameters of the purged water may be monitored. Parameters that are often monitored are pH, temperature, specific conductance, oxidation-reduction potential, dissolved oxygen and turbidity. Stabilization of these factors indicates that the purged water is representative of the formation water. Measurements are usually taken every three to five minutes and stabilization is achieved after all parameters have stabilized for a sufficient duration. The parameters will be considered stabilized if preferably about three successive readings are within plus or minus about 0.1 for pH, about 3% for conductivity, about 10 mV for redox potential, and about 10% for turbidity and dissolved oxygen.

The monitoring of the above parameters is a very useful tool in determining when the pump has begun to discharge samples representative of the formation water. However, determining when stabilization has been achieved is difficult, requiring continuous monitoring of multiple parameters and repeated calculations. Consequently, there exists the need for a device which can automatically monitor the parameters and provide notification when the selected parameters have stabilized.

SUMMARY OF THE INVENTION

It is a general object of the present invention to provide a method of monitoring purge water quality. It is another object of the present invention to provide a method for monitoring select purge water parameters.

In one preferred form, the present invention provides a method for monitoring select purge water parameters and determining when the parameters have stabilized. The method includes the steps of selecting which parameters are to be monitored and selecting the time interval between which evaluation readings are performed. The time interval may be selected in set time increments from within a predetermined time range. With the passing of each interval, the results of the evaluation readings are stored in a memory device for at least one, and more preferably a plurality, of consecutive readings. If the readings do not fall within the defined stabilization ranges for the selected parameters, the oldest scan is deleted from the memory device. The comparison of the reading results is again performed with the start of the next interval, with the new reading results being compared to the two old reading results. When the selected parameter values do fall within the defined ranges for three consecutive readings, the operator is alerted that stabilization has been obtained.

BRIEF DESCRIPTION OF THE DRAWINGS

Additional advantages and features of the present invention will become apparent from the subsequent description and the appended claims, taken in conjunction with the accompanying drawings, wherein:

DETAILED DESCRIPTION OF THE PREFERRED EMBODIMENT

Figure 1:
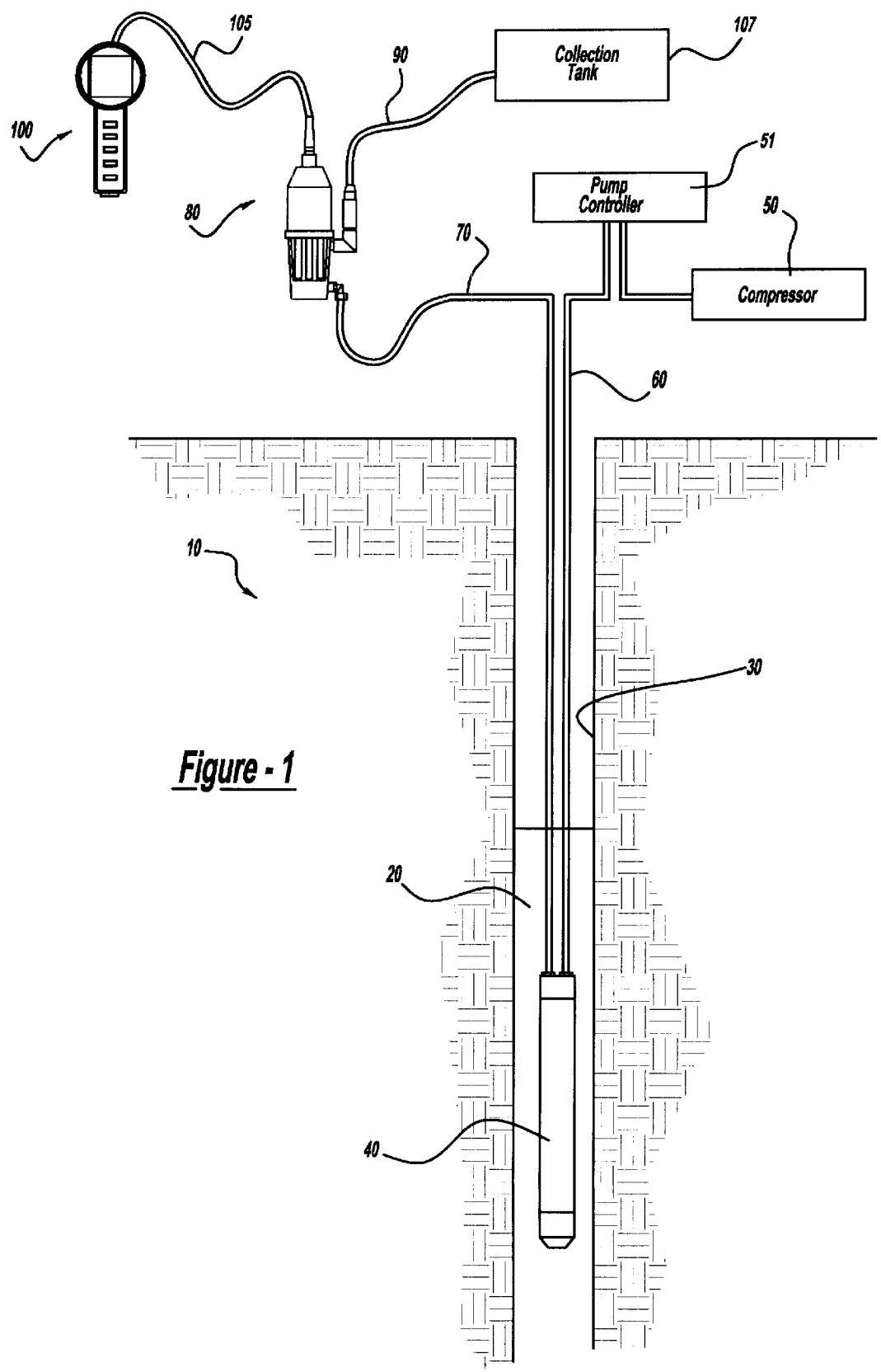
FIG. 1 is an illustration of a well containing a water pump, sensor assembly, and controller for monitoring purge water quality.

With initial reference to FIG. 1, a system 10 is illustrated for analyzing ground water in accordance with a preferred embodiment of the present invention. A volume of ground water 20 is contained in a well 30. The ground water 20 is pumped out of the well 30 by a pump 40 using low-flow techniques. The pump 40 purges the ground water 20 from the well 30 using compressed air obtained from a compressor 50 and delivered to the pump 40 through an air tube 60. A pump controller 51 controls the application of compressed air to the pump 40. The ground water 20 is purged through a water discharge tube 70 and directed to a sensor assembly 80. The sensor assembly 80 monitors select parameters of the ground water 20. Once the ground water 20 has been analyzed by the sensor assembly 80, the ground water 20 is directed out of the sensor assembly 80 by a second water discharge tube 90 which directs the ground water 20 to a collection tank 107. The sensor assembly 80 is operated by a controller 100 which displays the results of the parameter measurements. The sensor assembly 80 is connected to the controller 100 by way of a connector cable 105. Once three consecutive parameter measurements are obtained within predetermined stabilization ranges, the controller 100 alerts the operator that the parameters have stabilized. Upon stabilization, the water discharge tube 70 is disconnected from the sensor assembly 80 and the water discharged from the water discharge tube 70 is directed to a storage container for further analysis.

Figure 2:
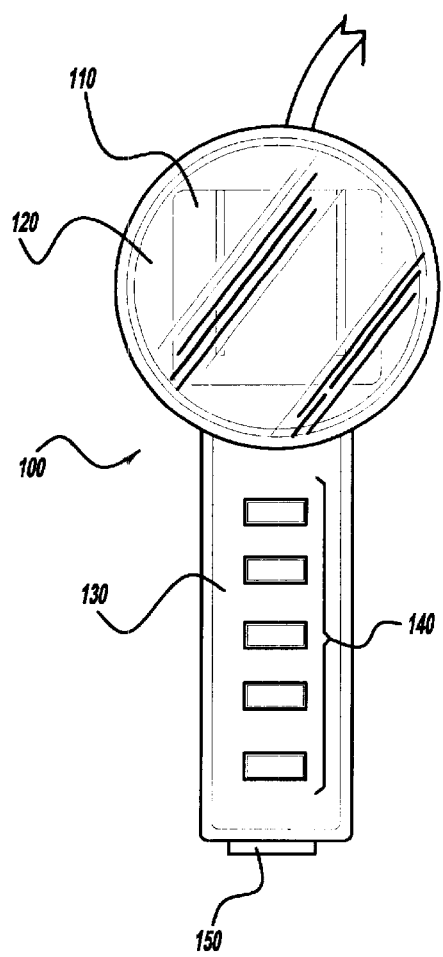
FIG. 2 is an illustration of the controller and its components.

FIG. 2 provides a more detailed view of controller 100. Controller 100 includes a liquid crystalline display 110 which displays the operation of the sensor assembly 80 and indicates to the operator when select ground water parameters have stabilized. The liquid crystalline display 110 is covered by a lens 120. The controller 100 additionally includes a keypad 130 having five operating buttons 140. The five operating buttons 140 include an enter button to execute actions of a blinking cursor displayed on the liquid crystalline display 110, an escape/circulator button which toggles the circulator on and off and functions to return the icon to the previous operation without executing an operation, a left/up button which is used to move the icon during menu operations, a down/right button which is also used to move the blinking icon during menu operations, and an on/off button used to power the controller 100 on and off. The controller 100 is powered by a battery which is contained under a battery cap 150.

Figure 3:
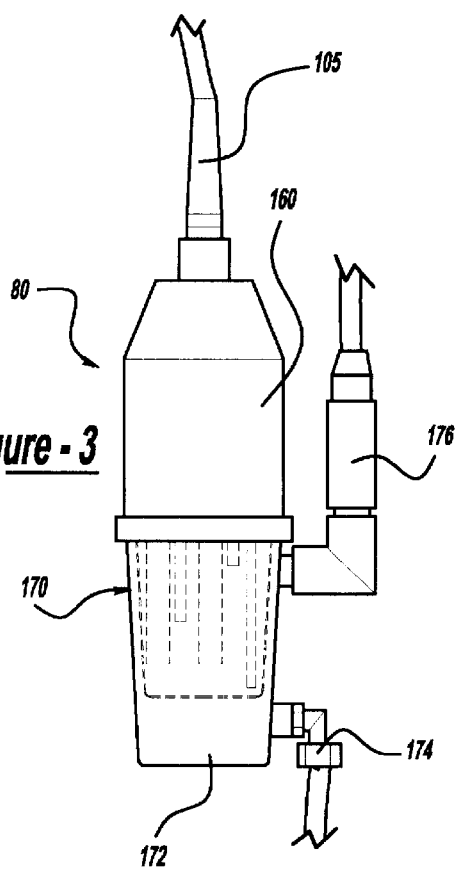
FIG. 3 is an illustration of the sensor assembly and its components.
Figure 4:
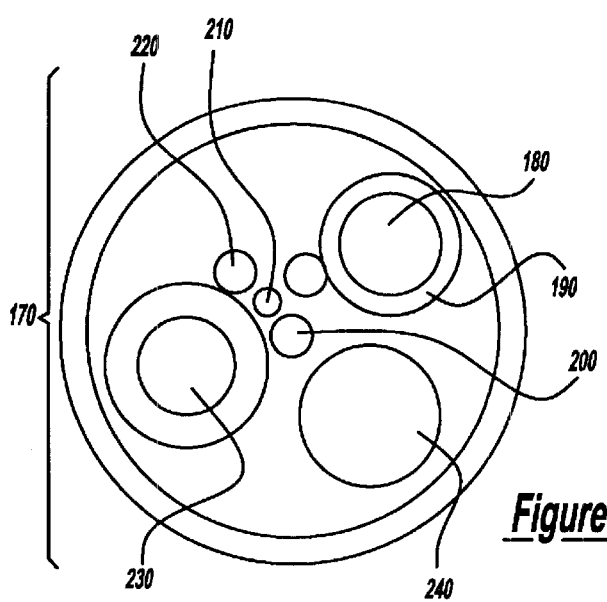
FIG. 4 is an expanded view of the sensor components of the sensor assembly.

FIGS. 3 and 4 provide a more detailed illustration of the sensor assembly 80. The sensor assembly 80 contains a housing 160 which contains a plurality of sensors 170 for monitoring select ground water parameters. The housing 160 contains a dissolved oxygen sensor 180, a specific conductance sensor 190, a temperature sensor 200, a oxidation reduction potential sensor 210, a pH sensor 220, and a reference sensor 230 used to calibrate the sensor assembly 80. The housing 160 also contains a circulator 240. The circulator 240 helps provide reliable dissolved oxygen measurements, continuously supplies fresh samples to the sensors, and keeps the sensors clean by sweeping away debris. Encompassing the sensors is a flow cell 172. The flow cell 172 contains an input valve 174 for receiving the ground water 20 fed through the water discharge tube 70 attached to the pump 40. The flow cell 172 also contains an output valve 176 connected to the second water discharge tube 90 which carries the ground water 20 from the sensor assembly 80 after it has been analyzed by the sensors 180–230.

Figure 5:
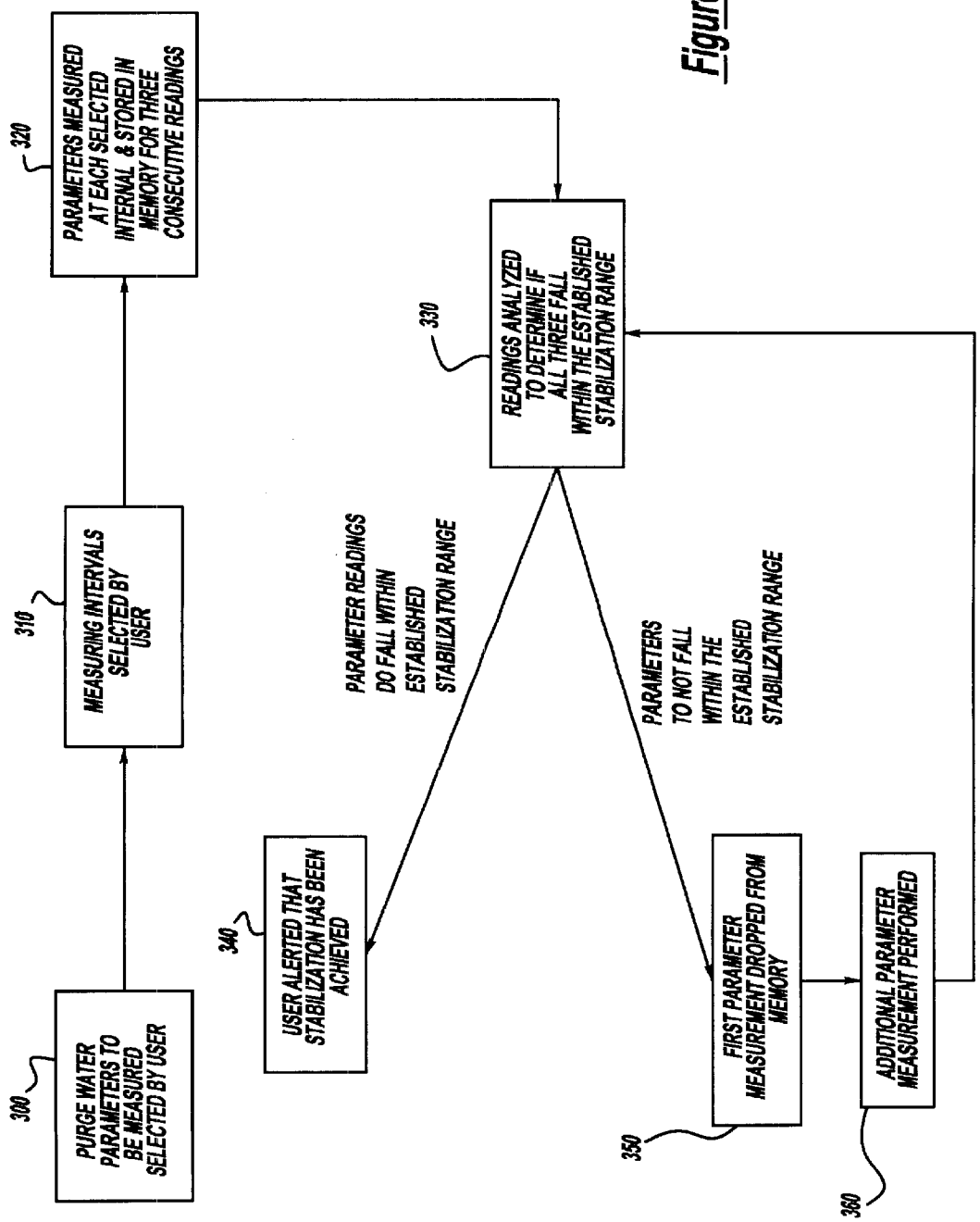
FIG. 5 is a flow diagram illustrating the method of monitoring the stabilization of the purge water parameters.

FIG. 5 is a flow diagram illustrating the method of monitoring the stabilization of the purge water parameters. At step 300, purge water parameters to be measured are selected by the user. The user may select to use one for more of the following four parameters: specific conductance, dissolved oxygen, oxidation-reduction potential, and pH. These parameters are measured using the sensors 180–230 attached to the housing 160 of the sensor assembly 80. Once the user has entered the parameters to be measured into the controller 100 using the operating buttons 140 on the keypad 130, the user selects the time interval between measurements of the selected parameters and enters the interval into the controller 100 as indicated at step 310. The interval may be selected in pre-selected time increments, such as one minute increments, from a range of preferably between about one to nine minutes. At step 320, the parameters measured at each selected interval are stored in the memory of the controller 100 for three consecutive readings. After three consecutive readings are preformed, the readings are analyzed by the controller 100 and visual information concerning the readings is displayed on the liquid crystalline display 110 of controller 100, as indicated at step 330. The parameter readings are analyzed to determine if they fall within the predetermined stabilization ranges. The stabilization range is preferably about 0.2 units for pH, about 0.2 mg/l for dissolved oxygen, about 0.020 mS/cm for specific conductance, and about 20 millivolts for oxidation reduction potential. It will be appreciated that the stabilization range for each of these factors could easily be made to be adjustable by suitable modifications to the controller 100 which enable the operator to select specific desired ranges for each of these factors.

If three consecutive readings are found to fall within the stabilization ranges, the user is notified that stabilization of the selected parameters has been achieved, as indicated at step 340. The user is alerted to the occurrence of stabilization through the liquid crystalline display 110 of the controller 100 and through audible tones produced by the controller 100. The occurrence of stabilization notifies the user that formation water is being produced by the pump 40. As a result, the user is able to obtain formation water samples by disconnecting the water discharge tube 70 from the sensor assembly 80 and collecting the formation water discharged in a suitable collection container. Alternatively, if additional data storage is employed, then essential continuous readings could be stored in a memory of the controller 100 for set time periods, and stabilization could be deemed to be achieved when all pertinent readings are with the desired ranges for a set period of time.

If three consecutive readings are not found to fall within the stabilization ranges, then the first measured parameter is deleted from the memory of controller 100, as indicated at step 350. At step 360, an additional parameter measurement is performed so that parameter measurements taken at three consecutive time intervals are again stored in the memory of the controller 100. After step 360, three consecutive readings are again analyzed, as indicated at step 330, to determine if they now fall within the established stabilization ranges. If the parameters do fall within the established stabilization ranges, the methodology again proceeds to step 340. If parameters do not fall within the established stabilization ranges then steps 350 and 360 are repeated before returning to step 330.

In addition to storing three consecutive measurements of the selected purge water stabilization parameters, the sensor assembly 80 preferably performs a full data scan which measures all current data values. The full data scan measures temperature, pH, dissolved oxygen, specific conductance, oxidation-reduction potential, salinity, total dissolved solids, elapsed time since the monitoring of the select stabilization factors was initiated, and circulator state. The results of the full data scan remain in the memory of the controller 100 regardless of whether the selected purge water parameters become stabilized or not. A full data scan is preferably performed at the point the command is given to initiate the monitoring of the selected purge water parameters and at selected time intervals, and preferably at about five minute intervals thereafter. Additionally, a full scan is performed for each of the three consecutive readings that result in satisfaction of the selected purge water parameter stabilization criteria.

It will be appreciated that the present invention provides an improved method and means for determining when measured water is representative of the formation water as opposed to stagnant water of the wellbore casing. The present invention provides the operator with an automated means for monitoring select purge water parameters and determining when the parameters have stabilized within values preset by the operator. Once the purge water parameters have stabilized within the preset parameters, the present invention alerts the operator that the water being measured is representative of the formation water as opposed to the stagnant water of the wellbore.

While the system and method of the present invention has been described as performing three consecutive measurements when monitoring water stabilization parameters, it will be appreciated that a greater or lesser plurality of successive measurements could be performed, depending on the desired accuracy to be attained. Also, it will be appreciated that the time intervals, ranges, and specific values recited in the forgoing description are exemplary values and could be easily modified as needed to tailor the system and method of the present invention to unique applications.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. A method for analyzing purge water parameters, the method comprising the steps of:
   collecting a volume of purge water from a subsurface source;
   selecting at least one purge water stabilization parameter to be measured;
   selecting a time interval between successive measurements of the purge water parameter;
   calculating the purge water parameter at each of the selected time intervals and storing the results for a plurality of measurement readings;
   comparing the results of the fixed consecutive measurement readings and determining whether each measurement reading thereof is within a desired stabilization range; and
   providing a signal when each said measurement reading of any given said fixed plurality of consecutive measurement readings are all within the desired stabilization range.

2. The method of claim 1, wherein the volume of purge water is collected using low-flow techniques.

3. The method of claim 1, wherein at least one of the following is measured as the purge water parameter: pH, dissolved oxygen, specific conductance, and oxidation reduction potential.

4. The method of claim 1, wherein the time interval between successive measurements of the purge water parameter may be selected in one minute increments.

5. The method of claim 1, wherein the selected time interval between successive measurements of the purge water comprises a time interval between from about one minute to about nine minutes in duration.

6. The method of claim 1, wherein the predetermined stabilization range comprises 0.2 units for pH, 0.2 mg/l for dissolved oxygen, 0.020 mS/cm for specific conductance, and 20 millivolts for oxidation reduction potential.

7. The method of claim 1, wherein said signal comprises an audible tone and a visual readout provided on a display of a controller.

8. The method of claim 1, wherein the volume of purge water collected is circulated through a sensor assembly containing a plurality of sensors.

9. The method of claim 8, wherein the plurality of sensors comprise sensors capable of measuring temperature, pH, dissolved oxygen, specific conductance, oxidation-reduction potential, salinity, and total dissolved solids.

10. The method of claim 1, wherein in the absence of the fixed consecutive measurement readings containing said measurement readings that are all within the desired stabilization range, an oldest one of said measurement readings thereof is deleted and a new measurement reading is added upon the expiration of a subsequent time interval.

11. The method of claim 10, wherein upon addition of the new measurement reading to said fixed plurality of consecutive measurement readings, the purge water stabilization parameter is recalculated to determine if it is within the desired stabilization range.

12. The method of claim 11, wherein in the absence of the fixed consecutive measurement readings containing said measurement readings that are all within the desired stabilization range, the process of deleting the oldest one of the measurement readings and adding a new measurement reading, upon the expiration of the subsequent time interval, is repeated until each one of said measurement readings within said fixed plurality of consecutive measurement readings falls within the desired stabilization range.

13. A method of analyzing purge water removed from a wellbore to ensure that the purge water is representative of formation water rather than stagnant water from within a well casing of the wellbore, the method comprising the steps of:
   collecting a volume of purge water from the wellbore;
   selecting at least one purge water stabilization parameter to be measured;
   selecting a time interval between successive measurements of the purge water parameter;
   calculating the purge water parameter at each of the selected time intervals and storing the results for a plurality of measurement readings;
   comparing the results of the fixed consecutive measurement readings and determining whether each measurement reading thereof is within a desired stabilization range; and
   providing a signal when each said measurement reading of any given said fixed plurality of consecutive measurement readings are all within the desired stabilization range.

* * * * *